US010222326B2

(12) United States Patent
Rasanen et al.

(10) Patent No.: US 10,222,326 B2
(45) Date of Patent: Mar. 5, 2019

(54) METHOD AND APPARATUS FOR DETERMINING SILOXANE CONTENT OF A GAS

(71) Applicant: TEKNOLOGIAN TUTKIMUSKESKUS VTT OY, Espoo (FI)

(72) Inventors: Jaakko Rasanen, Espoo (FI); Tuula Kajolinna, Espoo (FI); Mona Arnold, Espoo (FI)

(73) Assignee: QUALVISTA LTD., Helsinki (FI)

( * ) Notice: Subject to any disclaimer, the term of this patent is extended or adjusted under 35 U.S.C. 154(b) by 261 days.

(21) Appl. No.: 14/916,062

(22) PCT Filed: Sep. 2, 2014

(86) PCT No.: PCT/FI2014/050670
§ 371 (c)(1),
(2) Date: Mar. 2, 2016

(87) PCT Pub. No.: WO2015/028720
PCT Pub. Date: Mar. 5, 2015

(65) Prior Publication Data
US 2016/0195471 A1 Jul. 7, 2016

(30) Foreign Application Priority Data
Sep. 2, 2013 (FI) .................................. 20135884

(51) Int. Cl.
*B01D 53/02* (2006.01)
*G01N 21/3504* (2014.01)
(Continued)

(52) U.S. Cl.
CPC ......... *G01N 21/3504* (2013.01); *B01D 53/30* (2013.01); *G01J 3/0227* (2013.01);
(Continued)

(58) Field of Classification Search
CPC .. B01D 53/30; G01J 2003/104; G01J 3/0227; G01J 3/42; G01N 21/3504; G01N 33/0047
See application file for complete search history.

(56) References Cited

U.S. PATENT DOCUMENTS

| 4,382,071 A | 5/1983 | Otsuka et al. |
| 5,448,070 A | 9/1995 | Day et al. |

(Continued)

FOREIGN PATENT DOCUMENTS

| JP | 2003013078 | 1/2003 |
| JP | 2006098387 | 4/2006 |
| JP | 2010137468 | 6/2010 |

OTHER PUBLICATIONS

International Search Report for PCT/FI2014/050670, Completed by the Finnish Patent Office dated Dec. 4, 2014, 6 Pages.
Ignatov et al. Russian Chemical Bulletin, International Edition. 2003, vol. 52, pp. 1-9, "Thermodynamic and kinetic parameters of elementary steps in SiF4 gas-phase hydrolysis. Quantum-chemical and FTIR spectroscopic studies".
(Continued)

*Primary Examiner* — Christopher P Jones
(74) *Attorney, Agent, or Firm* — Brooks Kushman P.C.

(57) ABSTRACT

A method for determining siloxane content of a gas by non-dispersive infrared analysis including the steps of providing infrared light at a limited wave number band selected according to the absorption bands of the siloxanes, transmitting the infrared light at the limited wave number band to a volume of a gas to be analyzed, and detecting the intensity of the infrared light at the limited wave number band passed through the volume of a gas to be analyzed. The siloxane content is determined based on the absorption of the infrared light at the limited wave number band. Preferably, the limited wave number band lies in the range of 800 to 860 $cm^{-1}$.

8 Claims, 3 Drawing Sheets

(51) Int. Cl.
*G01J 3/42* (2006.01)
*G01J 3/02* (2006.01)
*B01D 53/30* (2006.01)
*G01N 33/00* (2006.01)
*G01J 3/10* (2006.01)

(52) U.S. Cl.
CPC ............ *G01J 3/42* (2013.01); *G01N 33/0047* (2013.01); *G01J 2003/104* (2013.01)

(56) References Cited

U.S. PATENT DOCUMENTS

2004/0045096 A1 3/2004 Mani et al.
2004/0184980 A1 9/2004 Atobe et al.
2010/0223015 A1 9/2010 Phillips et al.
2013/0193325 A1 8/2013 Phillips et al.

OTHER PUBLICATIONS

Kebukawa et al. Meteoritics & Planetary Science. 2009, vol. 44, pp. 545-557, "Rapid contamination during storage of carbonaceous chondrites prepared for micro FTIR measurements".

Leu et al. Surface and Coatings Technology 2003, vol. 174-175, pp. 928-932, "Diagnostics of hexamethyldisiloxane/oxygen deposition plasma".

Magni et al. Journal of Physics D: Applied Physics. 2001, vol. 34, pp. 87-94, "Oxygen diluted hexamethyldisiloxane plasmas investigated by means of in situ infrared absorption spectroscopy and mass spectrometry".

Raynaud et al. Plasma Processes and Polymers. 2005, vol. 2, pp. 45-52, "FTIR Plasma Phase Analysis of Hexamethyldisiloxane Discharge in Microwave Multipolar Plasma at Different Electrical Powers".

Japanese Office Action for Japanese Application No. JP2016-537356, dated Jun. 26, 2018, English Translation attached to original, All together 6 Pages.

METHOD AND APPARATUS FOR DETERMINING SILOXANE CONTENT OF A GAS

CROSS-REFERENCE TO RELATED APPLICATION

This application is the U.S. national phase of PCT Application No. PCT/FI2014/050670 filed on Sep. 2, 2014, which claims priority to FI Patent Application No. 20135884 filed on Sep. 2, 2013, the disclosures of which are incorporated in their entirety by reference herein.

FIELD OF THE INVENTION

The present invention relates to a method and an apparatus for measuring siloxane content of a gas by non-dispersive infrared analysis.

BACKGROUND OF THE INVENTION

Biogas is an important source of renewable energy. Biogas can be produced from organic matter by digestion e.g. at waste water treatment plants, waste treatment plants, and agricultural site anaerobic plants. It can also be collected from landfill sites. Thus, the term "biogas" is used in this document as a common term to refer to any of "biogas", "landfill gas", "digester gas", etc. The main components of biogas are methane $CH_4$ and carbon dioxide $CO_2$, and it typically also comprises small amounts of hydrogen sulphide $H_2S$, moisture, and siloxanes as impurities. The use of biogas as an energy source is based on energy-releasing combustion of the components thereof. Biogas is typically used as a fuel in gas engines, gas turbines, micro-turbines, and fuel cells producing electricity. It can be also be combusted to produce heat.

Siloxanes are semi-volatile organosilicon compounds, which are used in a number of industrial applications and in consumer products, such as cosmetics and lubricants. As a result of their wide use, a substantial amount of siloxanes ends up in landfills and sewage, where they volatilize into landfill gas or digester gas. Siloxanes in biogas are usually organosilicon compounds. A siloxane is a functional group in organosilicon chemistry with the Si—O—Si linkage.

The increasing interest in the production of biogas and renewable energy in waste management and sewage treatment has created significant concern about the presence of siloxanes in biogas. Siloxanes as gaseous compounds are not reactive or corrosive as such, but they form hard, abrasive silica as a deposit on various surfaces of the equipment wherein biogas is used. Such deposit also acts as a thermal and electrical insulator. This deposit can cause serious damages, such as fouling, corrosion, and lower energy output in the biogas utilization equipment.

Table 1 lists some siloxanes most commonly occurring in digester gas. Based on their molecular structure, siloxanes are commonly divided into linear (denoted with "L") and cyclic (denoted with "D") siloxanes. The siloxane concentration of biogas is generally in a range of 0-50 mg/m$^3$, typically below 10 mg/m$^3$.

TABLE 1

| Compound | Abbreviation | Boiling point, ° C. |
|---|---|---|
| Hexamethyldisiloxane | L2 | 107 |
| Octamethyltrisiloxane | L3 | 153 |
| Decamethyltetrasiloxane | L4 | 194 |
| Dodecamethylpentasiloxane | L5 | 245 |
| Hexamethylcyclotrisiloxane | D3 | 135 |
| Octamethylcyclotetrasiloxane | D4 | 176 |
| Decamethylcyclopentasiloxane | D5 | 211 |
| Dodecamethylcyclohexasiloxane | D6 | 245 |
| Trimethylsilanol | TMS | 99 |

According to the literature, the most common siloxanes in a landfill gas are D3, D4, D5, L2 and L3. In addition to siloxanes, the landfill gas also contains relatively large concentrations of silanol.

To reduce the above harmful effects of siloxanes, the siloxane content of biogas should be kept or made as low as possible. For example, biogas production plants typically comprise biogas purification systems where the detrimental siloxanes are removed from biogas by using various methods. Thereby, the siloxane content is lowered before the use of biogas as fuel e.g. in gas engines. The siloxane content of biogas may, however, vary at different locations and even at the same location during different periods. Therefore, continuous monitoring of the siloxane content before and/or after the purification system would be needed in order to optimize the operation of the siloxane removal equipment when it's cleaning effect changes or the siloxane content of the gas to be cleaned changes.

Injecting biogas to a natural gas pipeline is another example of applications where reliable siloxane content monitoring is required. Strict requirements are set for the quality of the biogas to be injected to the natural gas pipeline, necessitating accurate determination of the siloxane content in the biogas.

The need for monitoring siloxanes in gases is also recognized in plastics manufacture and semiconductor production industries where siloxane monitoring is needed especially in controlling the air quality in a clean room.

Traditionally, siloxane content in biogas is determined offline by taking a gas sample, which is analyzed in a laboratory. The methods used in sampling and laboratory analysis are slow and laborious, and there is a danger of losses in connection with sampling and storage. The methods in use today do not allow on-site monitoring and direct monitoring of the process equipment. The most common analysis methods are based on a combination of gas chromatography and mass spectrometry (GC/MS). When the siloxane contents of gases to be analyzed are as low as 0.1-5 ppm, high demands are made on the analysis method.

Spectroscopic analysis methods exist which are based on determining a complete IR spectrum of a sample and which allow a comprehensive analysis of the composition of biogas. By means of multicomponent analyzers base on e.g. FTIR (Fourier Transform Infrared) spectrometry, it is in principle possible to determine the concentrations of all significant gas components. An FTIR analyzer is, however, very expensive and complicated apparatus. Furthermore, its use as an online measurement device and the evaluation of the measurement results require long experience.

US 2010/0223015 A1 discloses a method for monitoring siloxane compounds in a biogas by FTIR spectrometry. A first absorption spectrum is generated based on a ratio of a first spectral measurement and a second spectral measurement. The first spectral measurement is from a non-absorptive gas having substantially no infrared absorption in a specified wavelength range of interest. The second spectral measurement is from a sample gas comprising the biogas. The method also includes the step of calculating a concentration of at least one siloxane compound in the biogas using a second absorption spectrum based on, at least, a first individual absorption spectrum for a known concentration of the at least one siloxane compound. The measurement equipment is complicated and expensive.

As a more simple and low-cost approach, JP 2006098387 A discloses an analyzer for measuring siloxane content of a gas by NDIR (Non-Dispersive Infrared) technique. The analyzer comprises a broadband IR source and an optical filter restricting the light interacting with a sample gas to be analyzed and a reference gas to a wave number range of 1250-770 $cm^{-1}$. Various siloxanes have their absorbance maxima within this wave number range, so the presence of siloxanes in the sample gas can be determined on the basis of detected absorption. However, in this wave number range the measurement result is also affected by many other components of biogas, such as moisture, carbon dioxide, methane, etc, the concentrations thereof being orders of magnitude higher than that of the siloxanes. Therefore, specific measures are needed to eliminate the influence of interfering gas components. This makes the analyzer complicated and the interpretation of measurement results challenging. For instance, a dehumidifier or a moisture analyzer is needed to eliminate the effect of moisture on the measurements. A specific detector system is used in the analyzer, which detects light in said wave number range of 1250-770 $cm^{-1}$ To summarize, there is a continuous demand in the market for technology enabling reliable, online analysis of siloxane content in gases, in particular in biogas, with reasonable costs.

PURPOSE OF THE INVENTION

The purpose of the invention is to provide a method and an apparatus for cost-effective and simple determination of siloxane content of a gas.

SUMMARY

According to a method aspect, the present invention is focused on a method for determining siloxane content of a gas by non-dispersive infrared analysis. By siloxane content is meant here the concentration of one or more siloxanes present in the gas to be analyzed. In some applications, it is sufficient to determine the overall siloxane content, comprising the overall concentration of all siloxane types present in the gas at issue. In some other applications, contents of various siloxane type of groups thereof can be determined. The gas to be analyzed by the method can be biogas. On the other hand, the method can also be used e.g. to analyze the siloxane content of a clean room air in semiconductor industry.

By non-dispersive infrared (NDIR) analysis is meant a specific, simple and cost-effective spectrometry technique based on the use of absorption of light at a narrow wave number (or wavelength) band selected on the basis of the absorption spectra of the compounds to be determined. NDIR spectrometry thus differs from both dispersive techniques where broadband light is dispersed into separate wavelength components, each of which are analyzed separately, and e.g. FTIR (Fourier Transform Infrared) spectrometry based on the use of an interferometer and complex computing of the measured raw data.

The method of the present invention comprises the steps of providing infrared light at a limited wave number band selected according to the absorption bands of the siloxanes; transmitting the infrared light at the limited wave number band to a volume of a gas to be analyzed; detecting the intensity of the infrared light at the limited wave number band passed through the gas to be analyzed; and determining the siloxane content on the basis of absorption of the infrared light at the limited wave number band.

Thus, the basic principle of the method is generally known in the field of NDIR analysis: infrared light is transmitted through a gas to be analyzed, and intensity thereof at a limited wave number band corresponding to the absorption bands of the siloxanes is detected. Decrease in the intensity is then used as an indication of the presence of siloxanes in the gas to be analyzed.

According to the present invention, the limited wave number band lies in the range of 800 to 860 $cm^{-1}$. By lying in said range is meant here that the maximum intensity of infrared light in the limited wave number band lies within this range, and that the energy of the infrared light used in the method is concentrated within said wave number range so that no significant amount of light energy used in the method lies outside this range. For example, when considering the intensity spectrum of the infrared light at said limited wave number band, the wave numbers at which the intensity is equal to or exceeds the half of the maximum intensity value preferably lie in said range of 800 to 860 $cm^{-1}$.

Limiting the infrared light used in the siloxane determination to said range provides great advantages in that the sensitivity of the method to other compounds present in the gas to be analyzed, e.g. a biogas, can be strongly reduced. One of such impurities affecting the siloxane determination e.g. in the broadband process of JP 2006098387 A is moisture. The absorption peaks of the siloxanes in this limited range are lower than e.g. those around the wave number 1000 $cm^{-1}$. However, the inventors have found that this lower absorption is compensated by the radically decreased sensitivity to e.g. moisture.

The volume of gas may be a stationary sample volume of a gas to be analyzed. On the other hand, it may be a volume through which the gas is led as a continuous through-flow.

One compound having absorbance in said wave number range and being often present in gases the siloxane content of which is to be determined is carbon dioxide. Thus, depending on the accurate location and width of the limited wave number band, it may be necessary to compensate the effect of carbon dioxide on the absorption of the infrared light. Therefore, in one embodiment, the method also comprises the step of providing the content of carbon dioxide in the gas to be analyzed, and the step of determining the siloxane comprises compensating the effect of carbon dioxide on the absorption of the infrared light at the limited wave number band. At the same time, also the carbon dioxide content itself may be determined.

Said providing the content of carbon dioxide may comprise receiving existing information on the carbon dioxide content. On the other hand, carbon dioxide content may also be determined in the present method itself. In one embodiment based on the latter approach, the step of providing the content of carbon dioxide comprises the steps of providing infrared light at a compensation wave number band selected according to the absorption bands of carbon dioxide, transmitting the infrared light at the compensation wave number band to the volume of the gas to be analyzed, detecting the intensity of the infrared light at the compensation wave number band passed through the gas to be analyzed, and determining the carbon dioxide content on the basis of absorption of the infrared light at the compensation wave number band. Determining also the carbon dioxide content by means of NDIR allows the use of the same equipment, i.e. the same light source and detector means, for both the limited wave number band and the compensation wave number band. Preferably, the compensation wave number band lies outside of the range of 800 to 860 cm$^{-1}$, i.e. outside the range in which the limited wave number band lies. This allows selection of the compensation wave number band so that the absorption by siloxanes does not significantly interfere with the carbon dioxide measurement. One example of suitable absorption peaks of carbon dioxide, according to which the compensation wave number band can be selected, is the absorption peak at 972 cm$^{-1}$.

In this document, the expression "on the basis of absorption" at the wave number band at issue means, naturally, that absorption at that particular band is used for determining the particular substance(s) at issue, e.g. siloxane(s) or carbon dioxide. However, it is important to note that said expression does not exclude the use of information on absorption at some other band within the range of 800 to 860 cm$^{-1}$ also. Thus, e.g. when determining the carbon dioxide content "on the basis of absorption of the infrared light at the compensation wave number band", also absorption at the limited wave number band (possibly with two or more sub-bands) may be taken into account. This applies also vice versa so that in the determination of the siloxane content, also the absorption at the compensation wave number band may be used. The accurate algorithm used for the actual determination of the contents of the different compounds can be adjusted according to the details of the wave number bands used the intensity measurements.

Similarly to carbon dioxide, also methane may be determined and taken into account in the determination of siloxane content by either receiving a ready determined methane content or by determining the methane content by means of another compensation wave number band.

Many of the most common cyclic and linear siloxanes have absorption bands in the wave number range of 800 to 860 cm$^{-1}$. Thus, in principle, any single limited wave number band lying within said range may be used to determine the siloxane content in the gas to be analyzed. However, due to the different absorption spectra of different siloxane types, the accuracy of the determination of the overall siloxane content may be strongly affected by the siloxane types present in the gas. For example, for the same concentration, a siloxane type with a low absorbance at the limited wave number band may result in much lower determined siloxane content than another siloxane type with stronger absorbance. Therefore, in one embodiment, the limited wave number band comprises a first sub-band and a second sub-band, and in the step of determining the siloxane content, the siloxane content is determined on the basis of absorption of the infrared light at the first and the second sub-bands. With an appropriate selection of the two sub-bands according to the absorption bands of the different siloxane types and with a suitable algorithm, it is possible to reliably determine the overall siloxane content. As an example, one of the sub-bands may cover essentially the entire range of 800 to 860 cm$^{-1}$, whereas the other sub-band may be narrower and adjusted to match some specific siloxane absorption band(s). It is also possible to use two narrow sub-bands, and also more than two sub-bands.

In addition to, or instead of the overall siloxane content, in some applications it is desired to know the partial contents of the cyclic and the linear siloxanes. Therefore, in one embodiment where two sub-bands are used, the step of determining the siloxane content comprises a step of determining the contents of the cyclic and the linear siloxanes on the basis of absorption of the infrared light at the first and the second sub-bands.

In principle, the infrared light at the limited wave number band can be produced by means of one or more narrow band light sources emitting at said band. As an alternative to this, in one embodiment the step of providing the infrared light at the limited wave number band comprises the steps of generating infrared light, with a possibly broad emission spectrum, and filtering the infrared light so as to limit it to the limited wave number band. This allows, for example, use of low-cost broadband thermal sources. On the other hand, the same broadband source can be used to produce light both at the limited wave number band and at the compensation wave number band.

Preferably, the step of filtering the infrared light is performed before the step of transmitting the infrared light at the limited wave number band to the volume of gas to be analyzed.

In the embodiments above, equipment and processes as such known in the art may be used. For example, infrared light at desired wave number bands may be produced and detected by known infrared sources, filters, and detectors. Known principles to form sample chambers may be used to implement continuous, on-line measurements. The measurements at the limited wave number band, possibly including the sub-bands, and at the possible compensation wave number band may be separated in space by using separate optical paths and detectors for each wave number band. Alternatively, they may be separated in time by measuring the intensity at different bands alternately. This can be implemented, for example, by using filters mounted on a rotating chopper wheel.

Determination of the siloxane content has many applications, in particular in various handling processes of biogas. In one embodiment, the method further comprises the step of producing, on the basis of the determined siloxane content, a control signal for controlling a biogas handling process which can be, for example, one of a biogas purification process, and a biogas injection process for injecting biogas into a natural gas pipeline. The control signal can be any signal for use in such process. For example, it can be a simple alarm signal indicating siloxane content exceeding a predetermined limit. Such alarm signal can then be used e.g. to stop injection of biogas or to adjust the operation of a purification apparatus. It can also be used to estimate maintenance cycles of equipment utilizing the analyzed biogas, such as gas engines, turbines, or fuel cells.

The method of the present invention may be carried out as a continuous on-line measurement along a gas process equipment, wherein the gas to be analyzed is led as a continuous flow from a gas pipeline to a measurement station and back.

What is stated above concerning the details and advantages of the method of the present invention applies, mutatis mutandis, also to the apparatus of the present invention discussed below. The same applies vice versa.

According to an apparatus aspect, the present invention is focused on an apparatus for determining siloxane content of a gas by non-dispersive infrared analysis.

The apparatus comprises a sample chamber for receiving a gas to be analyzed, preferably as a continuous through-flow for allowing online measurements where gas to be analyzed is led from a gas pipeline to a measurement station and back. On the other hand, the sample chamber can also be configured so as to form an integral part of an existing gas pipeline for allowing true on-line measurements.

The apparatus also comprises an illumination arrangement configured to produce infrared light at a limited wave number band selected according to the absorption bands of the siloxanes, and to transmit the infrared light at the limited wave number band through the sample chamber. The illumination arrangement can comprise one or more light sources and optics, e.g. lenses. Further, the apparatus comprises a detector for detecting the intensity of the infrared light at the limited wave number band passed through the sample chamber.

Finally, the apparatus also comprises at least one memory and at least one processor coupled with the memory, the memory comprising program code instructions configured to, when executed by the processor, cause the apparatus to determine the siloxane content on the basis of absorption of the infrared light at the limited wave number band. The memory and the processor can be implemented as an application-specific equipment, but they can also be parts of a standard computer.

In general, all the elements of the apparatus as defined above may be based on components and devices as such known in the art, especially in the field of NDIR spectrometry. Therefore, no detailed explanation thereof is given in this document. In addition to the elements specified above, a complete apparatus may naturally comprise also other components and elements, such as appropriate measurement electronics for carrying out controlling of the light source(s) and processing the signals measured by the detector.

According to the present invention, the limited wave number band lies in the range of 800 to 860 $cm^{-1}$. As discussed above in the context of the method of the present invention, this provides great advantages in improved determination accuracy and decreased cross-sensitivity to other compounds contained in the gas to be analyzed.

To take into account the effect of carbon dioxide on the infrared light absorption at the limited wave number band, the apparatus is preferably further configured to provide the content of carbon dioxide in the gas to be analyzed, wherein the program code instructions are configured to cause the apparatus to compensate the effect of carbon dioxide on the absorption of the infrared light at the limited wave number band. In one embodiment, the illumination arrangement is further configured to produce infrared light at a compensation wave number band selected according to the absorption bands of carbon dioxide and to transmit the infrared light at the compensation wave number band through the sample chamber; the detector is further configured to detect the intensity of the infrared light at the compensation wave number band passed through the sample chamber; and the program code instructions are configured to cause the apparatus to determine the carbon dioxide content on the basis of absorption of the infrared light at the compensation wave number band. Thus, in this embodiment the apparatus is configured to measure the infrared absorption both at the limited wave number band and at the compensation wave number band. These measurements are used to determine the siloxane content by taking into account also the carbon dioxide present in the gas. Preferably, the compensation wave number band lies outside of the range of 800 to 860 $cm^{-1}$ for preventing the siloxanes from interfering with the carbon dioxide content determination. The same light source(s) and detector(s) may be used for the both wave number bands.

In one embodiment, the limited wave number band comprises a first sub-band and a second sub-band, and the program code instructions are configured to cause the apparatus to determine the siloxane content on the basis of absorption of the infrared light at the first and the second sub-bands. In one particular embodiment based on such two sub-bands, the program code instructions are configured to cause the apparatus to determine the contents of the cyclic and the linear siloxanes on the basis of absorption of the infrared light at the first and the second sub-bands.

The illumination arrangement may comprise narrow-band infrared sources emitting at desired wave number bands. Alternatively, in one preferred embodiment, the illumination arrangement comprises a light source for generating infrared light in a possibly broad emission band, and a filter arrangement configured to filter the infrared light so as to limit it to the limited wave number band. Correspondingly, also the infrared light at the compensation wave number band can be produced by filtering initially broad-band light by means of a filter arrangement. The filter arrangement may thus comprise separate filters for the limited wave number band, possibly comprising the sub-bands, and for the compensation wave number band. The different filters may be mounted e.g. on a rotating chopper wheel, wherein the light transmitted to the sample chamber is alternately filtered to the limited wave number band and the compensating wave number band.

Preferably, the filter arrangement is configured to filter the infrared light before it is transmitted through the sample chamber. By filtering the infrared light before is enters the sample chamber, fluorescence and some other undesired effects possible caused by a broadband illumination can be avoided.

Instead of just determining the siloxane content, the apparatus may also comprise means for facilitating utilization of the determined siloxane content. In one embodiment, the program code instructions are further configured to cause the apparatus to produce, on the basis of the determined siloxane content, a control signal for controlling a biogas handling process. The biogas handling process may be, for example, a biogas purification process or a biogas injection process for injecting biogas into a natural gas pipeline. Such signal can be supplied to an automatic control system of such process. Alternatively, the signal can be used manually to adjust the processes on the basis of the control signal.

The apparatus may be further configured to provide the methane content of the gas to be analyzed, by receiving ready determined methane content, or by determining it similarly to the carbon dioxide content, by means of another compensation wave number band selected according to the absorption bands of methane.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION OF THE INVENTION

Figure 1:
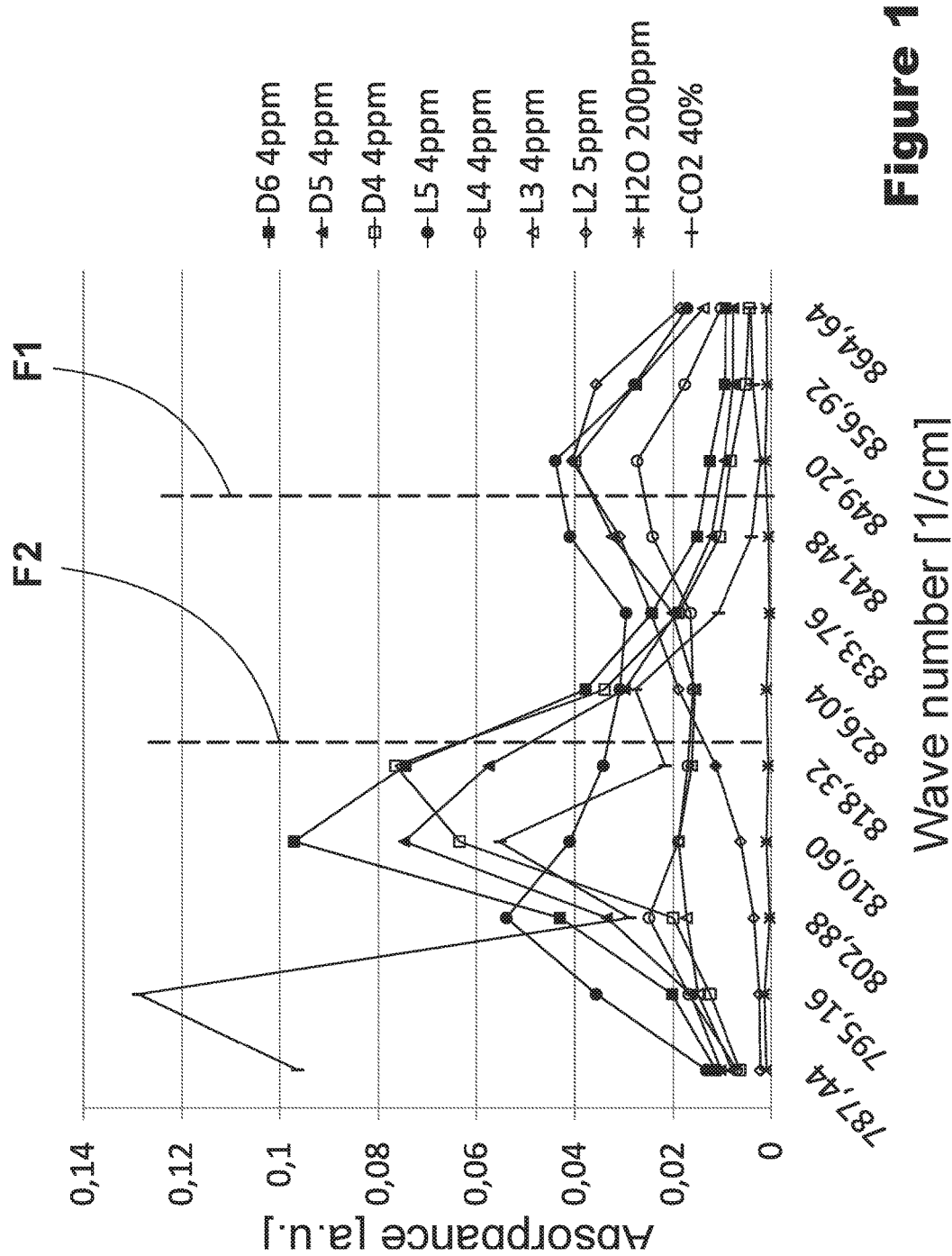
FIG. 1 shows the absorption spectra of various common siloxanes present in biogas in the wave number range of 800-860 cm-1.

FIG. 1 shows the absorption spectra of five commonly appearing siloxanes (L2, L3, L4, D4 and D5) with a concentration of 4 ppm in the wave number range of 800-860 cm$^{-1}$. It can be seen that each of those siloxane absorption spectra has at least one absorption peak at 800-850 cm$^{-1}$. Cyclic siloxanes D4 and D5 have the highest absorbance peak values. FIG. 1 also shows the absorption spectra of carbon dioxide with a concentration of 40%, methane with a concentration of 60%, and water with a concentration of 200 ppm. Those concentrations of the different siloxane types and carbon dioxide represent typical contents of those substances in biogas. The water content in biogas varies. 200 ppm used as an example in FIG. 1 is a typical content in biogas to be injected to a natural gas pipeline. On the other hand, purified biogas to be supplied to a gas engine typically comprises 1-2 volume percent of water $H_2O$.

It can be seen in FIG. 1 that in the wave number range of 800 to 860 cm$^{-1}$, carbon dioxide has significant absorption, whereas the absorption of water is much lower. Also methane has practically insignificant absorptance at this wave number band. This forms the basis for the present invention: despite the siloxane absorptances in this wave number range are clearly lower than those e.g. in the wave number range 1050-1100 cm$^{-1}$, the low sensitivity of absorption measurements to water and methane makes this wave number band surprisingly an excellent choice for determining the siloxane content of a gas, e.g. a biogas. Practically only $CO_2$ affects the absorption measurements and its effect can be compensated in the present invention as explained below.

FIG. 1 also illustrates examples of possible locations of the centers of two sub-bands F1, F2, together forming a limited wave number band, for use in the method according to the present invention.

Figure 2:
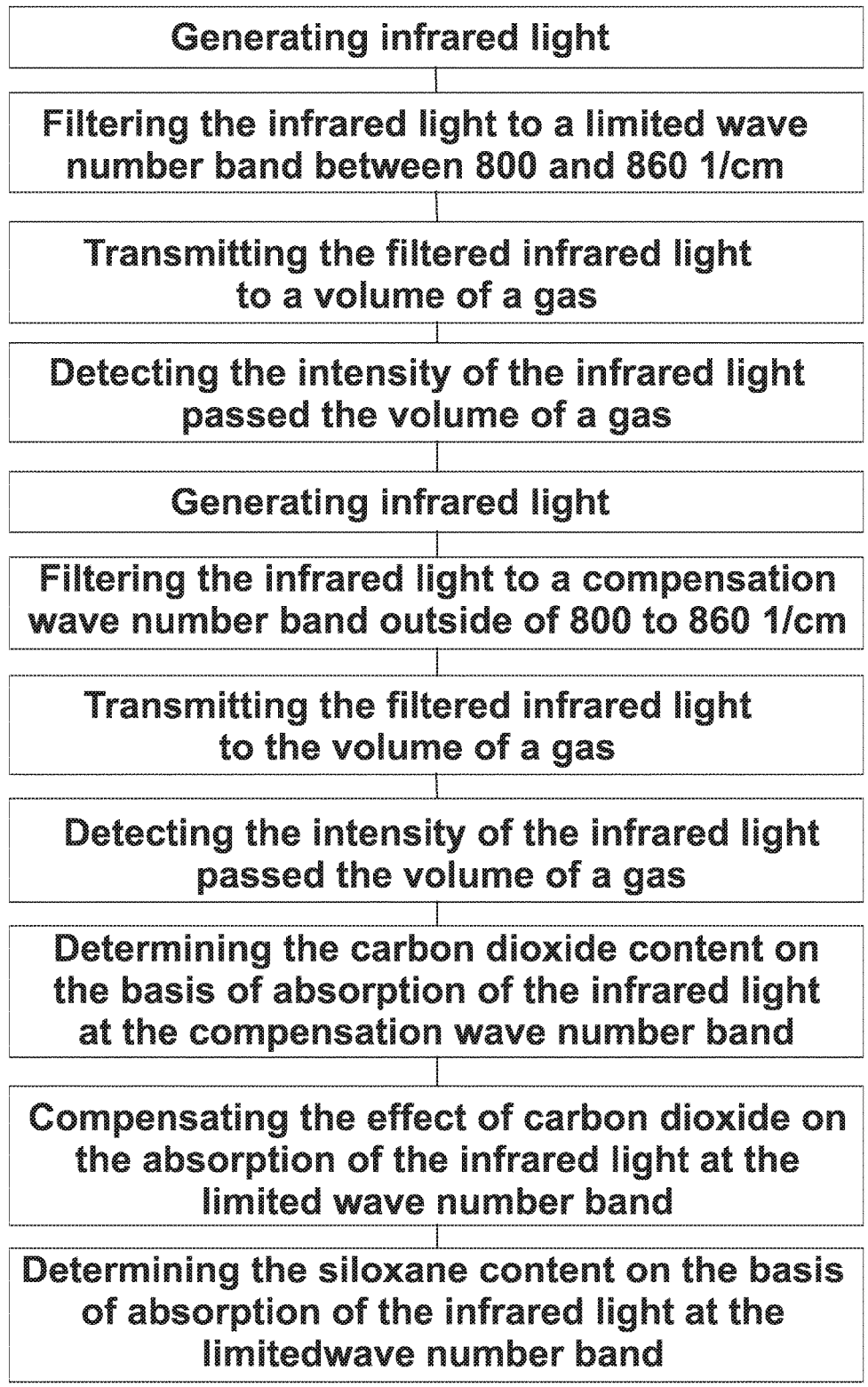
FIG. 2 illustrates as a flow diagram a non-dispersive infrared analyzation process according to the present invention.

The process illustrated in FIG. 2 starts by generating IR light and filtering it to a limited wave number band lying between 800 and 860 cm$^{-1}$. The filtered light is transmitted to a volume of a gas to be analyzed, and the intensity of the light passed through the volume of the gas is detected for investigating the absorption of the light by the gas. These steps may be repeated twice, once for a first sub-band and once for a second sub-band within said wave number range. Thereby two different intensity measurements at two different wave number bands are received.

Corresponding generation of IR light, filtering it, transmitting through the volume of the gas and detecting the intensity of the passed light is carried out also for a compensation wave number band selected according to the absorption bands of carbon dioxide outside of the range of 800 to 860 cm$^{-1}$.

The steps above can be performed using one single pair of a light source and a detector, by alternately filtering the light to the different wave number bands. In practice, this can be carried out e.g. by using a rotating chopper wheel on which the different band-pass filters are mounted.

The carbon dioxide content in the gas to be analyzed is then determined on the basis of absorption of the infrared light at the compensation wave number band. Based on this carbon dioxide content, the effect of carbon dioxide on the absorption of the infrared light at the limited wave number band is compensated, and the siloxane content of the gas is determined on the basis of absorption of the infrared light at the limited wave number band.

Finally, the determined siloxane content can be used to generate a control signal for controlling some biogas handling process (not illustrated in the drawing).

Figure 3:
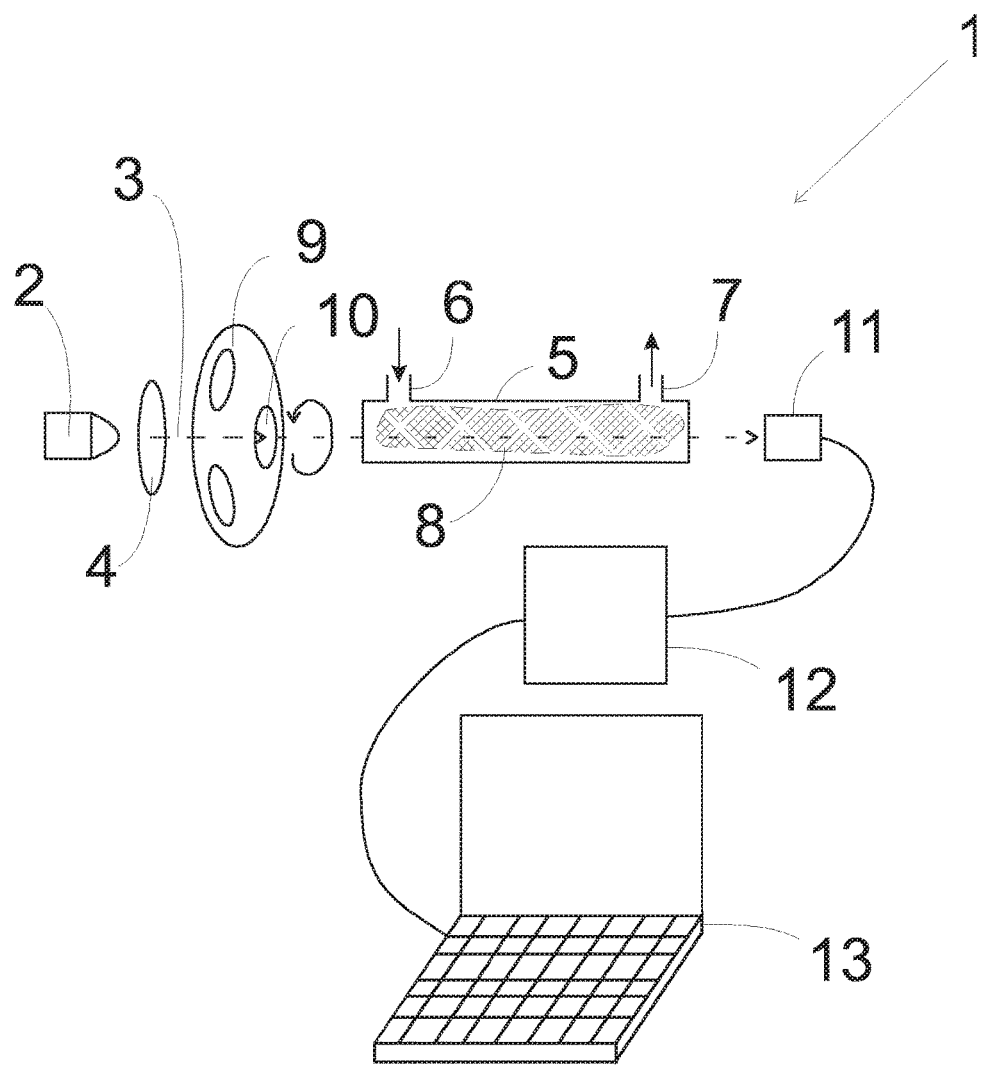
FIG. 3 shows as a schematic diagram a non-dispersive infrared analyzer according to the present invention.

The apparatus 1 of FIG. 3 comprises an infrared light source 2. This can be e.g. a thermal source, the operation of which is based on radiation of a heated body according to the Planck radiation law. One possibility for the material of such thermal source is silicon carbide SiC.

The light 3 emitted by the infrared light source is collimated by a lens 4 and directed towards a sample chamber 5 having an inlet 6 and an outlet 7 for supplying a gas 8 to be analyzed in the sample chamber. Between the sample chamber and the light source there is a rotating chopper wheel 9. Three narrow band-pass filters 10 are mounted on the openings of the chopper wheel. Thus, when the chopper wheel rotates, the light is alternately filtered by the three filters. At the same time, the light transmitted to the sample chamber becomes pulsed, enabling AC measurement of the light intensity.

Two of the filters have pass bands selected according to the absorption bands of the siloxanes in the range of 800 to 860 cm$^{-1}$. One filter has a pass band outside of this range, selected according to the absorption bands of carbon dioxide.

After having passed the sample chamber filled with a gas to be analyzed, the pulsed filtered infrared light is received by a detector 11 for detecting the light intensity and variations thereof. The intensity can be then compared with intensity values measured by using a reference gas not absorbing significantly in the pass bands of the filters in order to determine the intensity drop due to absorption by the gas to be analyzed. Of course, the reference gas can be also some gas mixture with precisely known content of compounds absorbing in those pass bands.

As one example, the two pass bands for siloxanes can be located with their peaks at about 820 and 845 cm$^{-1}$, and can have FWHM (Full Width at Half Maximum) values of 40 and 10 cm$^{-1}$, respectively. Thus, in this example, one of these two filters covers the major part of the whole range of 800 to 860 cm$^{-1}$, whereas the other, narrower filter is adjusted to the range where the linear (L-type) siloxanes have higher absorbances than the cyclic ones. By detecting the intensity at two sub-bands allows more accurately determination of the overall siloxane content, and also determination of the contents of the cyclic and the linear siloxanes and the relationship thereof. Alternatively, both of those two filters may have a narrow pass band, the two pass bands possibly partially overlapping. In general, it is important to note that the above wave number values are just examples only, and the actual filter performance can vary as long as the filters limit the infrared light in the limited wave number range of 800 and 860 cm$^{-1}$. It is also possible to use only one filter for the siloxanes. For examples, when testing the present invention, very good siloxane determination measuring performance was achieved by using single filter approach e.g. with filters with their transmission peak values at 818 and 819 nm, and FWHM values of 14 and 38 cm$^{-1}$.

The pass band of the filter for measuring carbon dioxide may be located anywhere where the absorption of the infrared light by siloxanes does not interfere too much with the carbon dioxide measurement. To avoid such interference, it is preferable to select the pass band filter for carbon dioxide clearly separate from the wave number range of 800 to 860 cm-1 used for measuring the siloxane absorption. As one example of this approach, the pass band filter for carbon dioxide can be adjusted to the local absorption peak at 972 cm$^{-1}$. Despite the separate wave number ranges, with sufficiently broad emission spectrum, the same light source can be used for both siloxane and carbon dioxide measurements.

The signals measured by the detector are processed by a measurement electronics unit 12. This processing may comprise e.g. amplifying and frequency filtering of the signals. For example, the electronics may comprise lock-in amplifier modulated by the chopper wheel rotation.

The processed signals are fed to a processor, represented by a lap top computer 13 in FIG. 3. A software is installed in the memory of the computer to cause the processor to determine, on the basis of the detected intensities at the three pass bands, the overall siloxane content in the gas as well as the partial contents of the linear and the cyclic siloxanes, taking into account also the effect of carbon dioxide on the decrease of detected intensity. Also the carbon dioxide content is thus determined.

As an optional feature, a control signal may be produced by the processor/computer for controlling some biogas handling process, e.g. biogas purification process, on the basis of the determined siloxane content(s).

It is essential to note that the illustration of FIG. 3 shows schematically some core elements of an apparatus for determining the siloxane content only. Naturally, the apparatus may comprise any other optical, mechanical, electronic and/or electrical means required in practice to implement a complete analyzer. Just as one example, there may be means for heating the gas to be analyzed before it is fed to the sample chamber, and for keeping the sample chamber at a constant temperature to avoid the influence of temperature fluctuations on the measurement results.

An apparatus as illustrated in FIG. 3 may be integrated, for example, as a part of a gas purification system, wherein siloxane can be determined by the apparatus continuously on site.

It is obvious to a person skilled in the art that with the advancement of technology, the basic idea of the invention may be implemented in various ways. The invention and its embodiments are thus not limited to the examples described above; instead they may vary within the scope of the claims. Just as one example of possible variations, instead of a continuously emitting infrared source and a rotating chopper wheel, pulsed infrared light can be also provided by means of an electrically modulated infrared source.

The invention claimed is:

1. An apparatus for determining siloxane content of a gas by non-dispersive infrared analysis, the apparatus comprising:
    a sample chamber for receiving a gas to be analyzed,
    an illumination arrangement configured to produce infrared light at a limited wave number band selected according to the absorption bands of the siloxanes, and to transmit the infrared light at the limited wave number band through the sample chamber,
    a detector for detecting the intensity of the infrared light at the limited wave number band passed through the sample chamber, and
    a memory and a processor coupled with the memory, the memory comprising program code instructions configured to, when executed by the processor, cause the apparatus to determine the siloxane content on the basis of absorption of the infrared light at the limited wave number band,
    wherein the limited wave number band lies in the range of 800 to 860 cm-i wherein the limited wave number band comprises a first sub-band and a second sub-band, and wherein the program code instructions are configured to cause the apparatus to determine the siloxane content on the basis of absorption of the infrared light at the first and the second sub-bands; and
    wherein the program code instructions are configured to cause the apparatus to determine the contents of cyclic and linear siloxanes on the basis of absorption of the infrared light at the first and the second sub-bands.

2. The apparatus as defined in claim 1, further configured to provide the content of carbon dioxide in the gas to be analyzed, wherein the program code instructions are configured to cause the apparatus to compensate the effect of carbon dioxide on the absorption of the infrared light at the limited wave number band.

3. The apparatus as defined in claim 2, wherein the illumination arrangement is further configured to produce infrared light at a compensation wave number band selected according to the absorption bands of carbon dioxide and to transmit the infrared light at the compensation wave number band through the sample chamber, the detector is further configured to detect the intensity of the infrared light at the compensation wave number band passed through the gas to be analyzed, and
    the program code instructions are configured to cause the apparatus to determine the carbon dioxide content on the basis of absorption of the infrared light at the compensation wave number band.

4. The apparatus as defined in claim 3, wherein the compensation wave number band lies outside of the range of 800 to 860 cm'.

5. The apparatus as defined in claim 1, wherein the illumination arrangement comprises:
    a light source for generating infrared light, and
    filter arrangement configured to filter the infrared light so as to limit it to the limited wave number band.

6. The apparatus as defined in claim 5, wherein the filter arrangement is configured to filter the infrared light before it is transmitted through the sample chamber.

7. The apparatus as defined in claim 1, wherein the program code instructions are further configured to cause the apparatus to produce, on the basis of the determined siloxane content, a control signal for controlling a biogas handling process.

8. The apparatus as defined in claim 5, wherein the biogas handling process is one of a biogas purification process, and a biogas injection process for injecting biogas into a natural gas pipeline.

* * * * *